(12) United States Patent
Fust

(10) Patent No.: US 6,344,210 B2
(45) Date of Patent: *Feb. 5, 2002

(54) COMPOSITION FOR FRESHENING NOSTRILS AND SINUS CAVITIES

(76) Inventor: Charles A. Fust, 313 S. Seaboard Ave., Venice, FL (US) 34292

(*) Notice: Subject to any disclaimer, the term of this patent is extended or adjusted under 35 U.S.C. 154(b) by 10 days.

This patent is subject to a terminal disclaimer.

(21) Appl. No.: 09/785,367

(22) Filed: Feb. 16, 2001

Related U.S. Application Data

(63) Continuation-in-part of application No. 09/585,070, filed on Jun. 1, 2000, which is a continuation-in-part of application No. 09/152,151, filed on Sep. 11, 1998, now Pat. No. 6,083,525, which is a continuation-in-part of application No. 09/123,646, filed on Jul. 28, 1998, now abandoned, which is a continuation-in-part of application No. 08/644,225, filed on May 10, 1996, now Pat. No. 5,785,988.

(51) Int. Cl.⁷ .................................................. A61F 13/00
(52) U.S. Cl. ........................................ 424/435; 424/434
(58) Field of Search .................................. 424/434, 435

(56) References Cited

U.S. PATENT DOCUMENTS

| | | |
|---|---|---|
| 1,804,670 A | 5/1931 | Brennan |
| 1,823,094 A | 9/1931 | Dylong |
| 2,237,954 A | 4/1941 | Wilson |
| 2,356,062 A | 8/1944 | Johnson .................... 167/65 |
| 2,660,166 A | 11/1953 | Coleman ................... 128/148 |
| 3,145,711 A | 8/1964 | Beber ....................... 128/148 |
| 3,457,917 A | 7/1969 | Mercurio ................... 128/140 |
| 3,463,149 A | 8/1969 | Albu ......................... 128/140 |
| 3,828,577 A | 8/1974 | Haynes ........................ 63/2 |
| 4,955,945 A | 9/1990 | Weick ....................... 128/203 |
| 5,175,152 A | 12/1992 | Singh ........................ 514/162 |
| 5,288,492 A | 2/1994 | Morris ...................... 424/195 |
| 5,378,465 A | 1/1995 | Zeines ...................... 424/195 |
| 5,489,435 A | 2/1996 | Ratcliff .................... 424/422 |
| 5,622,992 A | * 4/1997 | Beck ......................... 514/613 |
| 5,688,532 A | * 11/1997 | Bryce-Smith .............. 424/461 |

* cited by examiner

Primary Examiner—Thurman K. Page
Assistant Examiner—Rachel M. Bennett
(74) Attorney, Agent, or Firm—James W. Kayden; Thomas, Kayden, Horstemeyer & Risley

(57) ABSTRACT

A composition is disclosed for freshening sinus cavities, including a carrier of the ingredients and a masking agent for concealing or eliminating odors that emanate from the sinus cavities. The disclosure is also related to a composition for cleansing and freshening nostrils and sinus cavities that includes a saline solution as a moisturizing base component, a flavoring agent, a preservative, an antiseptic and/or antimicrobial agent, a counter-irritant, and an alcohol. The disclosure is also related to the use of such composition to provide many unexpected benefits of clean and healthy nasal and sinus passages.

25 Claims, No Drawings

COMPOSITION FOR FRESHENING NOSTRILS AND SINUS CAVITIES

CLAIM OF PRIORITY

This application is a continuation-in-part of co-pending U.S. Utility Application entitled, "Composition for Freshening Nostrils and Sinus Cavities," having Ser. No. 09/585,070, filed Jun. 1, 2000, which is a continuation-in-part of U.S. utility application having Ser. No. 09/152,151, filed Sep. 11, 1998, now U.S. Pat. No. 6,083,525, which is a continuation-in-part of U.S. utility application having Ser. No. 09/123,646, filed Jul. 28, 1998, now abandoned, which is a continuation-in-part of U.S. utility application having Ser. No. 08/644,225, filed May 10, 1996, now U.S. Pat. No. 5,785,988, which are entirely incorporated herein by reference.

FIELD OF THE INVENTION

This invention relates to a composition that is applied to a person's nostrils and sinus cavities, using an inhaler or other suitable means, for cleansing, freshening and deodorizing the named areas for controlling halitosis.

BACKGROUND OF THE INVENTION

Conventional control of halitosis or "bad breath", as it is often termed, is presently accomplished through the use of mouthwashes, breath mints, candy, chewing gum, brushing and flossing teeth, and other such means that are taken by mouth. Recent developments in this field have focused on the theory that the digestive organs can be responsible for objectionable odors that are produced from consuming certain foods or liquids.

Many problems have been associated with inadequate cleansing of the nasal and sinus cavities. For examples, smokers of cigars and cigarettes often have a particular form of fetid breath known as "smoker's breath." Further, other individuals suffering from problems associated with the nasal passages and sinus cavities become addicted to over-the-counter medicated nasal and sinus sprays. Active ingredients in these sprays alter normal body functions in order to achieve short-term results. Prolonged use of medicated sprays frequently results in user dependency. In many cases this occurs long after the original symptoms for which the sprays were intended have run their course.

Additionally, a particular type of fetid breath originates in an area deep within the throat, near the extreme rear of the tongue, where the sphenoid sinus drains into the throat. Bacteria buildup in this area produces sulfurous gases which results in accumulative fetid breath. Small plastic devices, described as tongue scrapers, are a common method people often use in an attempt to dislodge the bacterial build up as they attempt to combat this type of fetid breath; however, many of the users of these devices report vexatious retching with foreign objects placed so deeply within the throat.

Further, some individuals living in harsh, cold climates often associated with mountainous living, reported they frequently experience cracking and bleeding of the nasal passages. These same individuals reported their home interior heating is often very dry, resulting in a mild form of sleep distress.

Individuals living in certain parts of the country such as farm belts and urban suburbs frequently must contend with very high pollen concentrations contaminating the atmosphere. This environmental condition often results in distressed breathing among a great number of people because their airways become heavily taxed when the pollen, which resembles a very fine dust, becomes entrapped in their nose and sinuses. The pollen also results in sneezing and watery eyes.

Certain geographic areas, such as large, industrialized cities have very poor air quality due to high concentrations of airborne pollution caused by industrial and engine emissions, as well as common mold spores, dust and other hazardous particulates. The pollutants can lodge or even clog the nasal passages and sinus, possibly leading to infection.

Another problem associated with the sinuses is sinusitis, an infection of one or more of the sinus cavities, caused by fungus. Once infected, the lining of the sinus cavity becomes swollen, causing a buildup of fluid or mucus. This buildup is responsible for symptoms such as congestion, runny nose, headache pain and sinus pressure.

Not to be confused with chronic sleep disorders, some individuals snore due to obstructed nasal passages. The individuals who exhibit this condition also frequently experience an extreme dryness in their mouth. Much the same as with individuals seeking relief from snoring due to obstructed nasal passages, many other individuals have difficulty sleeping for the same reason "obstructed nasal passages".

A further possible problem with nasal and sinus passages is associated with the "common cold", a minor respiratory illnesses caused by a variety of different respiratory viruses. Symptoms of nasal discharge, nasal congestion and sneezing are usually present from the first day and usually progress to maximum severity by the second or third day. The cost of treatment with over-the-counter medications and outpatient clinics is estimated at more than $6.5 billion annually, all related to the relief of symptoms. The symptomatic treatment available often contains one or more antihistamines, decongestants, antitussives and expectorants, as well as other types of pharmaceutical actives. For individuals with certain medical conditions such as heart disease, hypertension, diabetes or thyroid disorder, these active ingredients could pose a risk.

In a wide range of respiratory infections, increased nasal secretion of mucus greatly reduces the efficiency of the sense of smell and taste, and also frequently creates the sensation of unusual taste and smell. This is sometimes reported as a "metallic effect". A heavy cold has a similar effect of damping odor sensitivity by the over-production of mucus and the swelling of the nasal membranes. A specific infection of the olfactory membrane, known as rhinitis, may result in an altered or total, temporary loss of smell. The same effect may stem from a number of allergies, all of which are associated with nasal congestion.

Other individuals having problems with nasal and sinus passages are those recovering from post operative medical care that are frequently required to visit an ear, nose and throat specialist (ENT) for sinus and nasal irrigation procedures. In these procedures, solutions are forced, under pressure, into the patient's affected areas for cleansing.

Some individuals who are required to communicate extensively, such as sales people and teachers, frequently experience excessive dryness of the mouth and nose. This dryness often results in unusual bad breath, as well as a soreness and discomfort of the throat.

Further, an altered sensitivity to odors is commonly encountered during pregnancy. Substances previously pleasant smelling may become repugnant to expectant mothers. The exact reason for this condition is not known, but the body's changed hormonal state exerts an influence on the olfactory membrane, frequently causing it to swell. Additionally, nasal blockage is commonly associated with pregnancy.

In today's market place, one can find health care products related to every conceivable hygienic purpose except for the nose and sinuses. For existing oral care products, what are often marketed as "new and improved formulas" are actually nothing more than old concepts. Mouthwash rinses are used to flush the mouth with bacteria killing agents and, in most cases, with additives of various types designed to freshen the mouth and mask odors. Bacterial elimination is normally accomplished by the use of alcohol and/or various dilutions of saline solution. The use of alcohol in these products often causes the intrusive effect experienced by many persons as a burning sensation. Saline solutions are very effective bacteria killing agents and do not cause the burning sensation; however, the taste is not well received by most consumers. While somewhat effective in some cases, mouthwashes and other oral means of controlling breath odors may not be completely effective in solving many of the problems noted above.

SUMMARY OF THE INVENTION

It is, therefore, one of the principal objects of the present invention to freshen breath and eliminate or mask objectionable breath odors by introducing the composition of the present invention into the nostrils and therethrough, into the sinus cavities.

Another object of the present invention is to provide a composition which may be conveniently introduced through the nose with, for example, an inhaler or atomizer-type container and which causes no discomfort to the user. A further object of the present invention is to provide an effective means of breath odor control as a substitute or supplement to conventional therapies and which has both immediate and residual effect.

These and additional objects are attained by the present invention which, in the broadest sense, comprises a carrier means, such as water or a dilute saline solution, and an odor masking agent. The odor-masking agent can be an essential oil or flavoring means such as those used in conventional mouthwashes. Other additives may include a small quantity of alcohol for acting on bacteria and an adherent means such as glycerin for maintaining the composition in place in the nostrils and sinus cavities for a sufficient length of time to produce the desired effect. Other means such as preserving agents and healing and soothing agents may also be employed.

Various additional objects and advantages of the present invention will become apparent from the following detailed description.

DETAILED DESCRIPTION OF THE PREFERRED EMBODIMENT

The present invention is a liquid composition that is inhaled through the nostrils and into the sinus cavities. It is of particular utility for use by persons who smoke cigarettes, cigars and the like, as the smoke necessarily invades the nostrils and sinus cavities when it is inhaled.

The composition includes a carrier means, which can be water or a mild or dilute saline solution. The saline solution is preferred and provides a mild antibacterial effect. Saline solutions are also commonly used as moisturizers at present and are safely used in the nasal passages and sinuses. While the concentration may vary between approximately 50% and approximately 75%, a solution of approximately 65% saline has been found to be effective and non-objectionable for the user.

Control and/or elimination of objectionable odors is accomplished using masking agents in the composition, such as, for example, but not limited to, oil of peppermint, spearmint, etc., or agents having a fruity or citrus essence. Other agents include, but are not limited to eucalyptol, methyl salicylate, and various other flavoring means.

A small quantity of alcohol may be used in the composition to provide an antibacterial effect. The alcohol is not necessary, but may facilitate mixing of the other components. A further component which may be added is a preserving agent such as benzalkonium chloride, which is used to extend shelf life. The use of the preserving agent or agents depends on whether or not some or any of the other components are stable in storage.

It is known in the art that zinc ions are powerful and natural antirhinoviral agents, immune system aids, interferon inducers, cell plasma/membrane pore closing agents, anti-inflammatory agents, antioxidants, protease inhibitors, and strong drying agents. It has been found that zinc ion availability (ZIA) values of approximately 100 will shorten the common cold by an average of seven days. Prior to the composition of present invention, ZIA 100 was only available in the form of zinc acetate lozenges. The composition of the present invention can also incorporate the ZIA 100 zinc acetate, or zinc chloride, thereby providing further healing and soothing properties to the composition. The zinc acetate or zinc chloride provided in the composition is pleasant tasting, flavor stable and causes no objectionable after taste.

Also included in the composition is an antiseptic and/or anti-microbial agent. Various embodiments of the composition exist in which various antiseptic and/or anti-microbial agents are used. In the preferred embodiment of the composition, the antiseptic agent used is cetylpyridinium chloride (CPC). Other antiseptic and/or anti-microbial agents include, but are not limited to, chlorhexidine digluconate, hexetidine, sanguinanine, triclosan, and benzalkoniun chloride. It should be understood that many other antiseptic and/or anti-microbial agents could be used in the present invention, as would be known to one skilled in the art.

The delivery method used for the composition can vary. Delivery means of the composition include for example, but are not limited to, spray bottles, droppers, and/or atomizer-type squeeze or pump bottles. Experimentation with a one ounce (1 oz.) pump atomizer spray bottle can be an effective delivery means of the composition. Containers of this type are currently used by several pharmaceutical companies for introducing sinus medication into the nostrils and sinus cavities. The atomizer-type bottles reduce the composition to a very fine mist, thus making the delivery of the composition minimally intrusive.

No discomfort for the user was experienced in testing of the composition. In addition, no harmful effects on the nostrils or sinus cavities were caused by any of the components of the composition. Further illustrated by clinicals entitled: "A Phase Study to Evaluate the Safety and Efficacy of SinoFresh Nasal Care Used Twice Daily" (the Study). The composition effectively eliminated or masked odors associated with smoking and with eating various foods such as onion, garlic and other spices, as well as certain liquids, particularly alcoholic beverages, coffee, tea, etc.

There are numerous advantages and unexpected results from use of the composition. For example, smokers and those exposed to second hand tobacco smoke who routinely use the composition of the present invention have all reported the complete elimination of smoker's breath. Many have also reported an improvement in their sense of smell after prolonged use of the composition.

Other than being the location of the olfactory membrane, the nasal cavity is quite unrelated to smells and smelling, but instead acts as an air-conditioning type system to clean and treat the air breathed before the air meets the sensitive and delicate tissues of the lungs. As such, it has been found unexpectedly that the sense of smell is improved by the cleansing of the olfactory hairs and the replacement of olfactory mucosa while using the composition of the present invention. Also, nose hairs become burdened with nicotine, tar and other tobacco-related chemicals. Routine hygienic cleansing of the nasal passages and sinus cavities aids the body in ridding itself of offensive odors, especially those that have become trapped in the middle, inferior and superior nasal concha. Freshening ingredients of the composition of the present invention that are left in the nose after cleansing with the composition leaves the nose and sinuses feeling cleansed, cleared, and refreshed with a minty aftertaste.

Many people have been able to substitute the use of the composition of the present invention in lieu of use of the medicated sprays, thereby relieving their dependency. Their unexpected results can be explained in several ways. First, the user develops a habit with regard to the sprayer itself. For example, some reformed smokers utilize a therapeutic device resembling a cigarette to imitate the act of placing an actual cigarette in their mouth. The use of the present composition fulfills a similar function for the user as use of stronger, harsher medicated sprays. Second, by keeping nasal passages and sinuses cleaner and therapeutically refreshed, users experience increased breathing capacity. This is especially beneficial because it is accomplished without the use of medicated ingredients. Therefore, the composition can be used as often as desired with absolutely no addictive problems.

Some individuals who use the composition have reported an unexpected improvement in oral-related fetid breath. Prolonged use of the composition allows for residual deposits of the cleansing and freshening agents to pass through the nasal and sinus passage and drain down into the described area of the mouth, thus resulting in correlative improvements in reducing these bacteria and deposits, and leaving behind freshening agents. The composition offers a more user-friendly approach to this type of bad breath.

While using the composition individuals living in harsh, cold climates that experience cracking and bleeding of the nasal passages reported a heretofore unprecedented tremendous improvement in the cracking and bleeding symptoms, as well as improvements in their sleep distress. These improvements are a result of moisturizing agents and isotonic saline nature of the composition ingredients. The sleep distress is relieved with a clearing of the nasal passages, which makes breathing easier in the thin atmosphere.

It is found unexpectedly that, with respect to those individuals living in areas with a high pollen count, routine hygienic cleansing of the nasal passages and sinuses with the composition, loosens and expels much of the pollen that has become trapped in the nasal passages and nose hairs which are acting as the body's filtering system for the respiratory system. The more the composition is used, the more pollen that is expelled. Because there are no medicinal ingredients in the composition, the user can cleanse the nose as often as necessary in order to relieve this type of problem.

For individuals living in polluted geographic areas, routine use of the composition can provide a previously unknown innocuous method of expelling much airborne pollution from the nose and sinuses. Use of the composition results in a cleansing and freshening process that improves breathing ability.

With respect to sinusitis, clinical studies were conducted to validate the use of the composition in the prevention and treatment of chronic sinusitis, the basis of which is the antifungal properties of the solution. In addition, it has been found unexpectedly that routine use will relieve many of the symptoms and bathe the affected area with soothing and antibacterial, anti-fungal, and/or anti-infective ingredients. Fetid breath is often present as an additional symptom of sinusitis that use of the composition can, in most cases, eliminate. Further illustrated by Clinicals entitled "Intranasal Antiseptic Effect on Chronic Sinusitis Protocol".

Individuals who snore, that regularly maintain good hygienic practices by utilizing the composition just prior to retiring to bed, report an unexpected and significant change in their ability to breathe clearly through the nose. With their change in breathing, they reported a decrease in oral dryness, thereby relieving the condition that is known to cause snoring.

The composition is also useful with resolving problems associated with the common cold. While the composition is not a cure for the common cold, many of the symptoms can be relieved without the need for medical or pharmaceutical ingredients. While the cold is "running its course", keeping the nose and sinuses clean, bathed and refreshed with minty, freshening ingredients helps the individual feel and breathe much better. Engaging in a thorough hygienic cleansing just prior to retiring for bed and after arising, thereby expelling excess nasal and sinus mucus that cause a "runny nose", brings tremendous relief to the user. Further, as noted previously, by raising the ZIA values in individuals suffering from the outset of a cold, the composition can shorten the duration of the cold.

For those individuals suffering from difficult breathing during sleep, many users of the composition have reported, unexpectedly, that they breathe much better after a thorough, hygienic cleansing of the nose and sinuses just prior to retiring to bed. Nasal mucus and other related foreign matter that has accumulated in the nose hairs is easily expelled with the therapeutic process. The user retires with clearer nasal passages and a refreshed, minty aftertaste and is less likely to experience sleep disorders associated with blocked nasal passages.

Further, within the scope of their ENT's complete approval, some of the users of the composition have utilized a method of hygienic cleansing of the nose and sinuses to compliment the care received at the ENT's office after surgery on the nose and/or sinus passages. The ingredients contained in the composition are completely innocuous, i.e., there is nothing present that will interfere with the physician's care. Unexpectedly, these users reported their breathing became easier, their nose and sinuses felt cleaner and very positive changes occurred in what they described as "very fetid" breath. The composition cannot be substituted for an ENT's care and hygienic cleansing of the nose and sinuses cannot be compared to, nor achieve the same results, as physician-supervised irrigation, no more than toothpaste and mouthwash can be substituted for procedures performed by a dentist in their office; nonetheless, the invention provides advantages to the user that do not come without its use.

With regard to individuals whose occupations require extensive verbal communication, unexpected results indicate that users of the composition have been able to restore moistness to their noses and sinuses and during routine use, residual amounts of the ingredients pass through the nose and sinuses, leaving deposits of the cleansing, freshening agents to soothe the throat.

With respect to pregnant women, users of the composition with this condition described as hormonal change have reported that routine cleansing of the nasal passage and sinuses seemed to improve their ability to breathe, likely due to the expulsion of the nasal blockage in the form of excess nasal mucus. The freshening ingredients left behind results in a minty aftertaste which can also often replace the sense of repugnant odors that may come with pregnancy.

The composition is truly an exception since it is in fact a new concept in the control of fetid breath. Prior to the invention, the effect the nose and sinuses have on a person's breath was not addressed. In addition, few people have considered the positive health benefits that can be achieved with routine therapeutic cleansing of the nose and sinuses.

If one examines an air filter, taken from the average home interior heating and cooling system, the debris caught in the filter clearly reflects samples of the many contaminants we ingest into our noses on a daily basis. If these filters were never cleaned, eventually the system would shut down. Because the nose and sinuses provide a similar function for our respiratory system, the positive benefits that can be achieved by routine cleansing is apparent.

The routine, hygienic cleansing of the nose and sinuses, using the composition containing isotonic saline, moisturizing, purifying and antiseptic agents will result in cleaner, healthier nasal and sinus passages, rewarding the user with an improved breathing ability. Unexpected results reveal that users of the composition have reported relief of many types of symptoms, likely due to their routine programs of hygienic cleansing of the nose and sinuses. After thorough cleansing, the deposits of freshening ingredients left behind replaces the metallic effect with a minty aftertaste.

EXAMPLE 1

The following formula provides a representative example of the composition.

| Ingredient | Amount |
| --- | --- |
| Sodium chloride | 0.65% |
| Benzalkonium chloride | 0.002% |
| Thimerosal | 0.001% |
| Eucalyptol | 0.03% |
| Methyl salicylate | 0.02% |
| Menthol | 0.015 |
| Alcohol | 0.07% |
| PEG or glycerin | Trace (Optional) |
| Zinc acetate/zinc chloride | Optional |

A summary of the properties of ingredients of the composition:

| Ingredient | Property |
| --- | --- |
| Sodium chloride | Base ingredient also acting as a moisturizer |
| Benzalkonium chloride | Preservative |
| Thimerosal | Preservative |
| Eucalyptol | Flavoring Agent, also containing antiseptic effect |
| Methyl salicylate | Counterirritant, (Local Analgesic containing flavor similar to Wintergreen) |
| Menthol | Counterirritant |
| Alcohol | Aids in solubility effect of other ingredients also containing antibacterial effect |
| Zinc acetate/zinc chloride | Healing and soothing properties |

The above listed formula for the composition has undergone testing and has proved effective for its stated purpose. The composition was dispensed from a 1 oz. pump atomizer bottle and was successful in eliminating and/or masking odors which could be considered offensive in certain circumstances or by certain people, i.e., odors from smoking, cutting, dicing, or consuming onions, etc.

Based on experiments that have been conducted, the eucalyptol, methyl salicylate and menthol can be replaced by other similar acting ingredients to completely change the flavor. The base ingredients of the composition, preservative (s) and alcohol, are in percentage amounts that will remain relatively constant. The solution of the invention is prepared according to known techniques and excipients, as described in "Remington's Pharmaceutical Sciences Handbook," $17^{th}$ ed., Hack Publ. Co., N.Y., U.S.A.

It should be stated that the composition of the invention is not limited to the ingredients stated in the original application or an intervening continuation-in-part (CIP) formulation. Substitution ingredients are widely available for each of the essential components, as described in "Remington's Pharmaceutical Sciences," $17^{th}$ edition.

The first set of intrinsic ingredients of the composition is the antiseptic and anti-infective agents. The elimination of certain types of fungus and bacteria, which are known to cause offensive odors, will aid in the freshening of the breath and are selected and formulated to produce the results as described.

The second set of intrinsic ingredients of the composition is the aromatic components which aid in the freshening and deodorizing of the nasal and sinus cavities. These ingredients are selected and formulated to produce the results described herein.

The third intrinsic ingredient of the composition is the isotonic, aqueous solution, acting as an osmotic agent. This ingredient is selected and formulated for the isotonic value and fully disclosed in "Remington's Pharmaceutical Sciences," $17^{th}$ edition. This ingredient is selected and formulated to produce the results further described herein.

EXAMPLE 2

The following formula provides a second representative example of an isotonic, sterile, aqueous solution of the composition. In this formula, the function of the ingredients is given under "Application".

| RANGE | INGREDIENT | APPLICATION | PERCENTAGE |
|---|---|---|---|
| 0.1 to 2% | Sodium chloride | Osmotic agent | 0.650 |
| 0.1 to 5% | Sodium borate | Buffering agent | 0.100 |
| 0.1 to 9% | Alcohol SD | Solubilizing agent | 0.090 |
| 0.001 to 2% | Edetate disodium | Preservative | 0.050 |
| 0.1 to 3% | Glycerin | Solubilizing agent | 0.001 |
| 0.001 to 5% | Polysorbate 80 ™ | Surfactant | 0.045 |
| 0.001 to 5% | Poloxamer 407 ™ | Antiseptic | 0.030 |
| 0.001 to 5% | Domiphen bromide | Antiseptic | 0.030 |
| 0.001 to 5% | Cetylpyridinium chloride | Anti-infective/Anti-Fungal | 0.040 |
| 0.1 to 2% | Sorbitol | Sweetener | 0.002 |
| 0.1 to 2% | Sodium saccharin | Sweetener | 0.002 |
| 0.1 to 5% | Aromatic component | Masking agent | 0.005 |
| 0.001 to 5% | Zinc acetate/zinc chloride | Healing agent | 0.040 |
| | Deionized water | Solvent (vehicle) | <100% (W/W %) |

The examples of the composition given, both in the parent application and the CIP filings, are representative of preferred embodiments. However, the ranges of the composition should not be limited to these examples in terms of ingredients and administration.

Thus, while an embodiment and various modifications thereof of the composition for cleansing and freshening nostrils and sinus cavities has been described in detail herein, various additional changes and modifications may be made without departing from the scope of the present invention.

I claim:

1. A composition for freshening sinus cavities comprising;
a carrier means;
an antiseptic/anti-fungal means; and
a masking agent for concealing or eliminating odors emanating from the sinus cavities.

2. A composition as defined in claim 1 and further including a preservative.

3. A composition as defined in claim 1 and further including a counterirritant.

4. A composition as defined in claim 1 and further including a solubility enhancer.

5. The composition of claim 1, wherein the antiseptic/anti-fungal means is selected from the group consisting of: cetylpyridinium chloride (CPC), chlorhexidine digluconate, hexetidine, sanguinanine, triclosan, and benzalkonium chloride.

6. A composition as defined in claim 1 and further including an anti-infective means.

7. A composition as defined in claim 1 and further including a healing agent.

8. A composition as defined in claim 7, the healing agent is selected from thegroup consisting of: zinc acetate and zinc chloride.

9. The composition as defined in claim 7, wherein the healing agent has a zinc ion availability of 100.

10. A composition as defined in claim 1, wherein the composition is dispensed through a delivery means selected from the group consisting of: a spray bottle, a dropper, a pump bottle, and an atomizer-type bottle.

11. A method, comprising the steps of:
providing a composition, wherein the composition includes
a carrier means,
an antiseptic/anti-fungal agent, and
a masking agent for concealing or eliminating odors emanating from the nasal passages or sinus cavities; and
using the composition by dispensing the composition in nasal passages or sinus cavities.

12. The method of claim 11, wherein the step of providing a composition that includes an antiseptic/anti-fungal agent comprises the step of providing a composition that includes an anitseptic/anti-fungal agent that eliminates bacteria, fungus and germs, thereby aiding in the control of bad breath and repression of allergy-related or sinusitis conditions.

13. The method of claim 11, wherein said method eliminates smoker's breath.

14. The method of claim 11, wherein said method acts as a placebo for medicated nasal compositions.

15. The method of claim 11, wherein said method soothes nasal and sinus passages of individuals living in harsh climates.

16. The method of claim 11, wherein said method cleans nasal and sinus passages of individuals living in areas with high pollen count.

17. The method of claim 11, wherein said method cleans nasal and sinus passages of individuals living in polluted areas.

18. The method of claim 11, wherein said method clears nasal and sinus passages of individuals that snore.

19. The method of claim 11, wherein said method clears nasal and sinus passages of individuals suffering from sleep arena.

20. The method of claim 11, wherein said method cleans nasal and sinus passages of individuals who have recently undergone nasal or sinus surgery.

21. The method of claim 11, wherein said method moisturizes nasal and sinus passages of individuals who communicate extensively verbally.

22. A composition for freshening nostrils and sinus cavities comprising a saline solution as a moisturizing base component, a flavoring agent for masking or eliminating odors from the sinuses or nostrils, a preservative means for enhancing the shelf life of the composition, a counterirritant for facilitating acceptance of the composition by the nostrils and sinuses, an infection preventative agent, and an alcohol for facilitating solubility of the components.

23. A composition as defined in claim 22 and further comprising a healing means.

24. A composition as defined in claim 23, wherein the healing means is zinc acetate or zinc chloride.

25. A composition comprising:
an osmotic agent of approximately 0.1 to approximately 2 percent by weight of the composition;
a buffering agent of approximately 0.1 to approximately 5 percent by weight of the composition;
a solubilizing agent of approximately 0.1 to approximately 12 percent by weight of the composition;
a surfactant of approximately 0.001 to approximately 5 percent by weight of the composition;
an antiseptic of approximately 0.001 to approximately 10 percent by weight of the composition;
an anti-infective/anti-fungal of approximately 0.001 to approximately 5 percent by weight of the composition;
a sweetener of approximately 0.1 to approximately 4 percent by weight of the composition;
an aromatic component of approximately 0.1 to approximately 5 percent by weight of the composition;
a healing agent of approximately 0.001 to approximately 5 percent by weight of the composition;
a solvent of less than approximately 100 percent by weight of the composition.

* * * * *